(12) United States Patent
Wu et al.

(10) Patent No.: US 10,919,878 B2
(45) Date of Patent: Feb. 16, 2021

(54) MCT4 INHIBITORS AND USES THEREOF

(71) Applicant: CHARLES R. DREW UNIVERSITY OF MEDICINE AND SCIENCE, Los Angeles, CA (US)

(72) Inventors: Yong Wu, Los Angeles, CA (US); Jay Vadgama, Los Angeles, CA (US); Zhimin Huang, Los Angeles, CA (US); Ke Wu, Los Angeles, CA (US)

(73) Assignee: CHARLES R. DREW UNIVERSITY OF MEDICINE AND SCIENCE, Los Angeles, CA (US)

( * ) Notice: Subject to any disclaimer, the term of this patent is extended or adjusted under 35 U.S.C. 154(b) by 0 days.

(21) Appl. No.: 16/395,099

(22) Filed: Apr. 25, 2019

(65) Prior Publication Data

US 2019/0352282 A1    Nov. 21, 2019

Related U.S. Application Data

(60) Provisional application No. 62/662,637, filed on Apr. 25, 2018.

(51) Int. Cl.
*C07D 403/04*    (2006.01)
*C07D 235/16*    (2006.01)
*C07C 233/66*    (2006.01)
*A61P 35/00*    (2006.01)

(52) U.S. Cl.
CPC ............ *C07D 403/04* (2013.01); *A61P 35/00* (2018.01); *C07C 233/66* (2013.01); *C07D 235/16* (2013.01)

(58) Field of Classification Search
CPC .................................................. C07D 403/04
See application file for complete search history.

(56) References Cited

FOREIGN PATENT DOCUMENTS

GB        1226438 A       3/1971
WO    2014/189152 A1    11/2014

OTHER PUBLICATIONS

PubChem CID 121074246, National Center for Biotechnology Information. PubChem Database. CID=121074246, https://pubchem.ncbi.nlm.nih.gov/compound/121074246 (accessed on Apr. 8, 2020), create date Jun. 17, 2016. (Year: 2016).*
Chemical Abstracts Registry No. 1360287-51-9, indexed in the Registry file on STN CAS Online Mar. 7, 2012. (Year: 2012).*
Chemical Abstracts Registry No. 1413088-00-2, indexed in the Registry file on STN CAS Online Dec. 10, 2012. (Year: 2012).*
Of Chemical Abstracts Registry No. 1413494-42-4, indexed in the Registry file on STN CAS Online Dec. 11, 2012. ( Year: 2012).*
Patent Cooperation Treaty, International Search Report and Written Opinion issued in PCT/US2019/029192, dated Feb. 27, 2020, pp. 1-13.
Steffen et al., Discovery and Structure—Activity Relationships of Modified Salicylanilides as Cell Permeable Inhibitors of Poly (ADP-ribose) Glycohydrolase (PARG), J Med Chem., Jun. 21, 2011, pp. 5403-5413, (54(15).
Takeuchi et al., On the Antimicrobial Activity and Syntheses of Carbanilide and Salicylanilide Derivatives, Yakugaku Zasshi, 1982, pp. 1023-1030, 102(11), English Abstract.
Hamada et al., On the Antimicrobial Activity and Syntheses of Salicylanilide Derivatives, Yakugaku Zasshi, 1981, pp. 633-641, 101(7), English Abstract.
Mikhailitsin et al., Search for new antiparasitic agents. 7. The study of anthelmintic activity-structure relatinships in new halogen-containing benzamides, Meditsinskaya Parazitologiya i Parazitarnye Bolezni, 1991, pp. 53-55.

* cited by examiner

*Primary Examiner* — Laura L Stockton
(74) *Attorney, Agent, or Firm* — Pillsbury Winthrop Shaw Pittman, LLP

(57) ABSTRACT

Presented herein are MCT4 inhibitors and uses thereof for treating cancer.

9 Claims, 11 Drawing Sheets

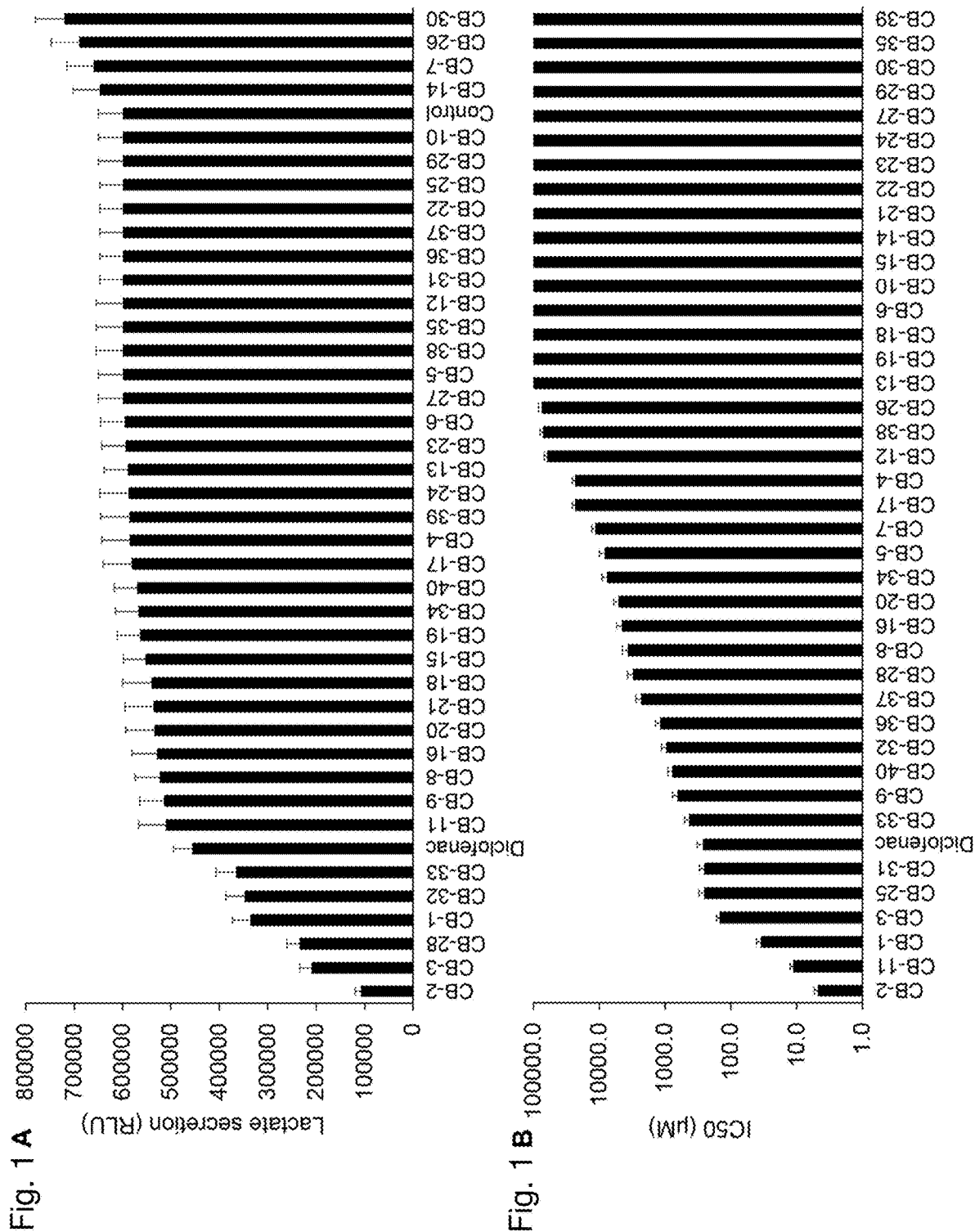

A  CB-3 (9235786) IC50 149.3 nM

1. # 9235786

N-(3,5-difluorophenyl)-N'-(4-{[6-(1H-imidazol-1-yl)-4-pyrimidinyl]amino}phenyl)urea Formula.................$C_{20}H_{15}F_2N_7O$
Molecular Weight.................407
LogP.................2.93
LogSW.................-4.67
Rotatable Bonds.................5
Hdon.................3
Hacc.................4
tPSA.................96.8
Form.................Solid

B

CB-1 (5175277) IC50 35.3 nM

1. # 5175277

Formula..................$C_{23}H_{13}BrCl_2INO_3$
Molecular Weight..........629
LogP......................9.27
LogSW....................-11.12
Rotatable Bonds...........4
Hdon......................2
Hacc......................3
tPSA......................58.6
Form......................Solid
Price group...............0

Show me analogs: 2D | 3D | 2D&3D

N-{2-[(1-bromo-2-naphthyl)oxy]-5-chlorophenyl}-5-chloro-2-hydroxy-3-iodobenzamide

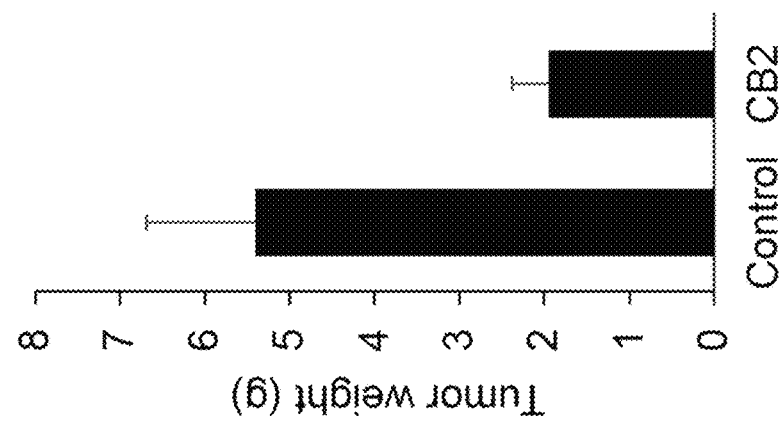
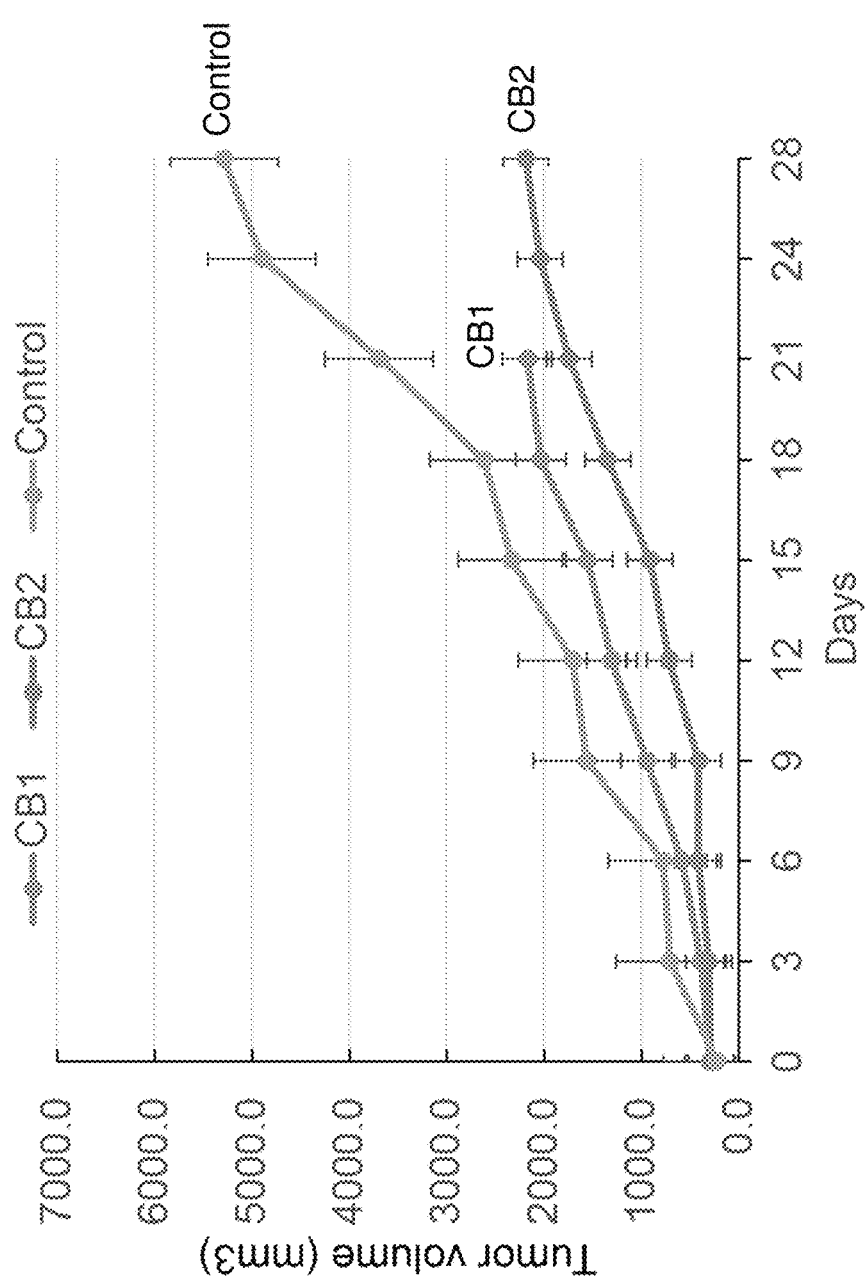
Fig. 8A
Fig. 8B

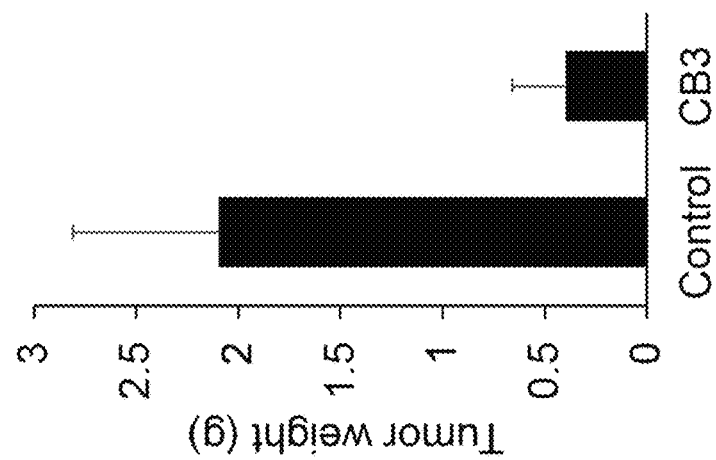
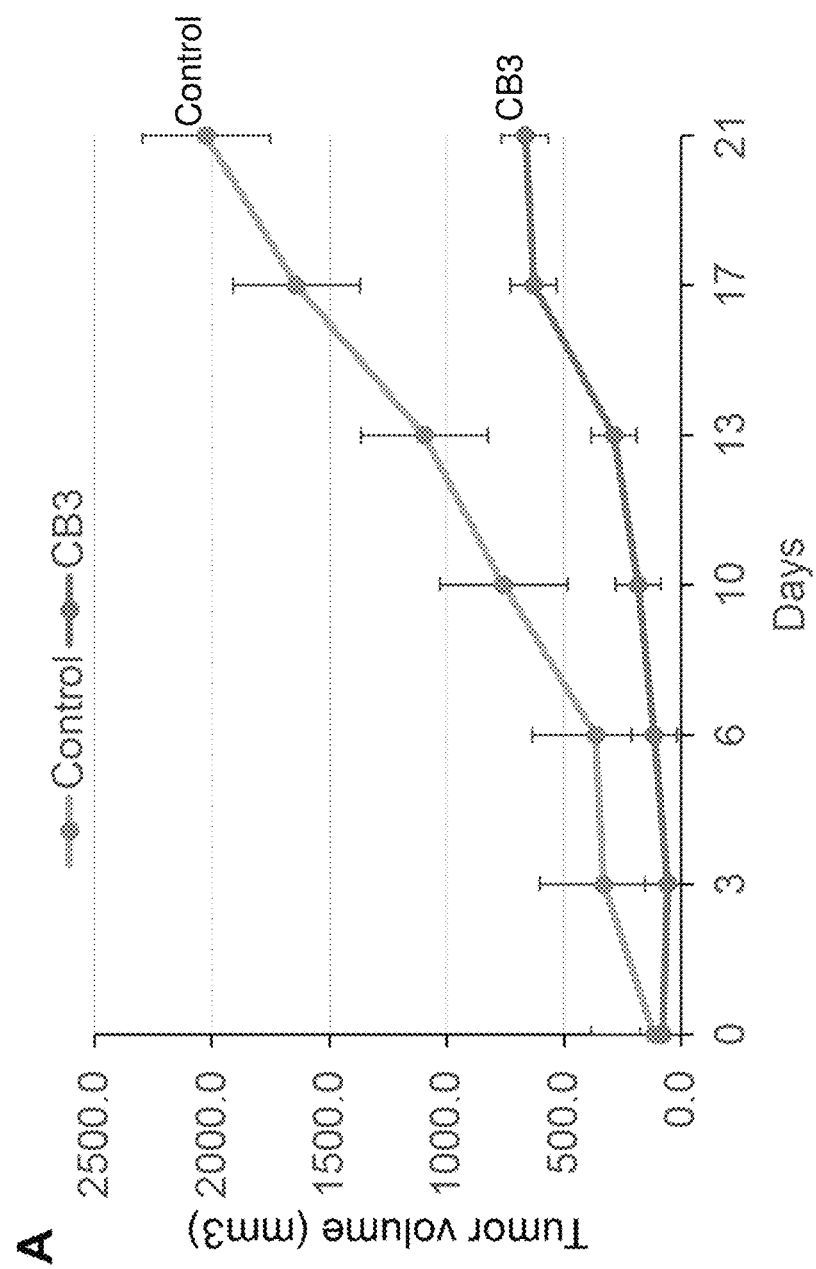

MCT4 INHIBITORS AND USES THEREOF

RELATED PATENT APPLICATIONS

This patent application claims the benefit of U.S. Provisional Patent Application No. 62/662,637 filed on Apr. 25, 2018, entitled NOVEL MCT4 INHIBITORS AND USES THEREOF, naming Yong Wu, Jay Vadgama, Zhimin Huang and Ke Wu as inventors.

FIELD OF THE INVENTION

Embodiments relate to novel inhibitors of monocarboxylate transporter 4 (MCT4), and uses thereof for treating cancer.

INTRODUCTION

Monocarboxylate transporter 4 (MCT4, also known as SLC16A3) is a cell-surface expressed monocarboxylate transporter. MCT4 is thought to catalyze the rapid transport of many monocarboxylates such as lactate, pyruvate, branched-chain oxo acids derived from leucine, valine and isoleucine, and the ketone bodies acetoacetate, beta-hydroxybutyrate and acetate, across the plasma membrane. MCT4 expression is highly up-regulated in many cancers, and its expression correlates with poor survival, in many cancer indications.

Upregulation of aerobic glycolysis and a high demand for ATP is common in many cancer types, a phenomenon known as the Warburg effect. Cancer cells typically import massive amounts of glucose which are funneled through an overactive glycolysis metabolic pathway. The excessively produced pyruvate is then converted to large amounts of lactate by the activity of the LDH enzyme. It is speculated that cancer cells upregulate the expression of cell-surface MCT4 to manage with the secretion of excessively produced lactate and to prevent intracellular acidosis. MCT4 silencing has been shown to repress and/or ablates tumor growth in xenograft models of breast cancer, colorectal cancer, and glioma.

Presented herein are novel MCT4 inhibitors and uses thereof to treat cancer.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A-B shows representative screening results of selected MCT4-targeting candidate compounds using MDA-MB-231 cells in vitro that reveals candidate compounds that markedly inhibiting MCT4 activity and cell proliferation. Briefly, MDA-MB-231 cells were incubated with the various compounds (2.5 µM) for 48 h followed by a lactate secretion assay. FIG. 1A shows that certain potential MCT4 inhibitors induced various levels of lactate secretion inhibition as measured by a LACTATE-GLO™ Assay. CB-2, CB-3 and CB-28 were the most effective. FIG. 1B shows the results of an assay to screen for the growth inhibitory effects of 40 MCT4 blocking candidates (y-axis shows IC50 values (µM)). The assay revealed varying inhibitory effects on cell proliferation, with CB-2, CB-11 and CB-1 having the most profound inhibition (IC50: 4.8, 11.3 and 35.3 µM, respectively). Small compound names are shown on the x-axis. Diclofenac was used as a positive control.

FIG. 8A-C shows the results of a mouse xenograft tumor model where mice were implanted with MDA-MB-231 cancer cells ($5 \times 10^6$ cells injected subcutaneously) and treated with CB-1, CB-2 or control. FIG. 8A shows a graph of tumor volume (y-axis) over time (i.e., Days, x-axis) for mice treated with CB-1, CB-2 or control. FIG. 8B shows tumor weight (g) for mice treated with CB2 or control. FIG. 8C shows mouse body weight (y-axis) over time (Days) for mice treated with CB-1, CB-2 or control. The results show that treatment with CB-1 or CB-2 inhibits tumor growth in vivo. Values represent mean±SD, n=6-8 mice/group.

FIG. 9A-C shows the results of a mouse xenograft tumor model where mice were implanted with MDA-MB-231 cancer cells (5×10⁶ cells injected subcutaneously) and treated with CB-3 or control. FIG. 8A shows a graph of tumor volume (y-axis) over time (i.e., Days, x-axis) for mice treated with CB-3 or control. FIG. 8B shows tumor weight (g) for mice treated with CB3 or control. FIG. 8C shows mouse body weight (y-axis) over time (Days) for mice treated with CB-3 or control. The results show that treatment with CB-3 inhibits tumor growth in vivo. Values represent mean±SD, n=8 mice/group.

DETAILED DESCRIPTION

Figure 2A:
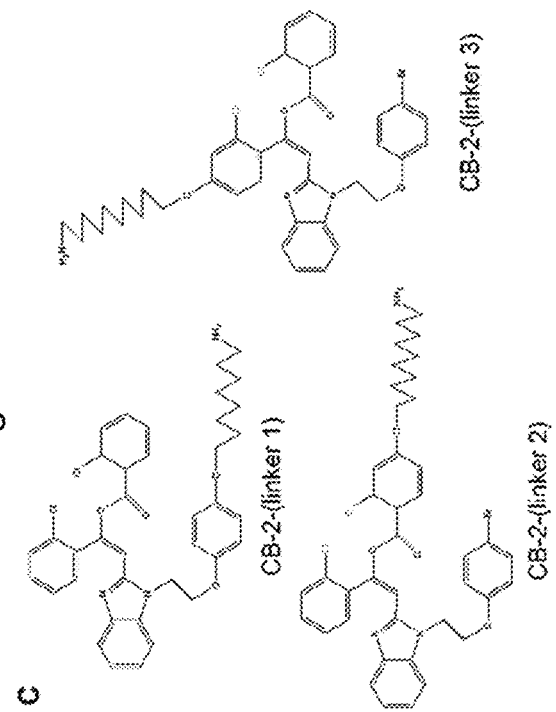
FIG. 2A shows the chemical structure of 2-{1-[2-{4-bromophenoxy)ethyl]-1H-benzimidazol-2-yl}-1-(2-chlorophenyl)vinyl 2-chlorobenzoate (CB-2).

Presented herein are compositions comprising an MCT4 inhibitor, and uses thereof for treating cancer.

MCT4 Inhibitors

Novel MCT4 inhibitor compound were identified herein by a combination of structure-based virtual screening and in vitro cell-based analysis.

In some embodiments, an MCT4 inhibitor is a compound, or a salt thereof, having the structure of formula I below:

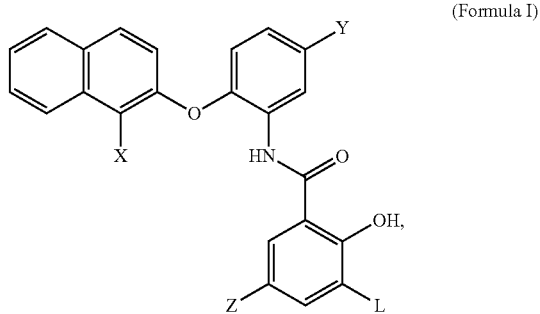

(Formula I)

wherein X, Y, Z and L are independently selected from hydrogen, chlorine, fluorine, bromine and iodine. In some embodiments, Y and Z of formula I are chlorine, X is Bromine and L is Iodine. In some embodiments, an MCT4 inhibitor is N-{2-[(1-bromo-2-naphthyl)oxy]-5-chlorophenyl}-5-chloro-2-hydroxy-3-iodobenzamide represented by formula Ia below:

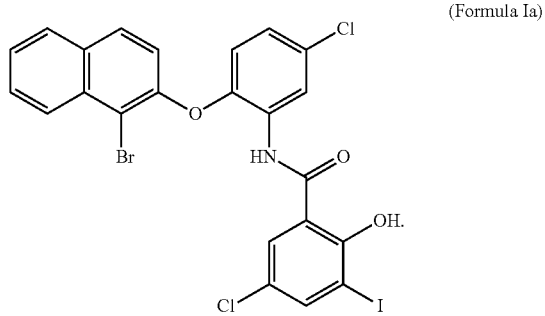 [SMILES: O=C(Nc1cc(Cl)ccc1Oc1ccc2ccccc2c1Br)c1cc(Cl)cc(I)c1O]

(Formula Ia)

The compound of Formula Ia is sometimes referred to herein as CB-1.

In some embodiments, an MCT4 inhibitor is a compound, or a salt thereof, having the structure of formula II below:

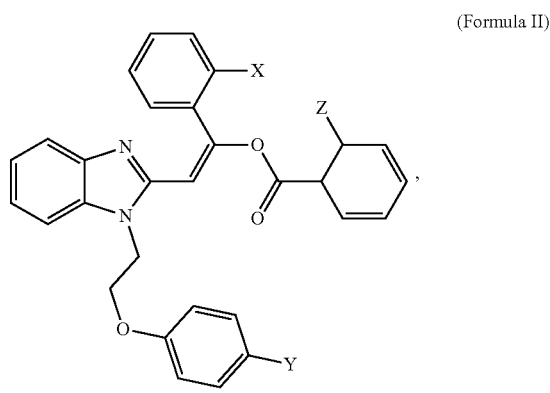

(Formula II)

wherein X, Y and Z are independently selected from hydrogen, chlorine, fluorine, bromine and iodine. In some embodiments, X and Z of formula II are chlorine, and Y is bromine. In some embodiments, an MCT4 inhibitor is 2-{1-[2-(4-bromophenoxy)ethyl]-1H-benzimidazol-2-yl}-1-(2-chlorophenyl)vinyl 2-chlorobenzoate represented by formula IIa below:

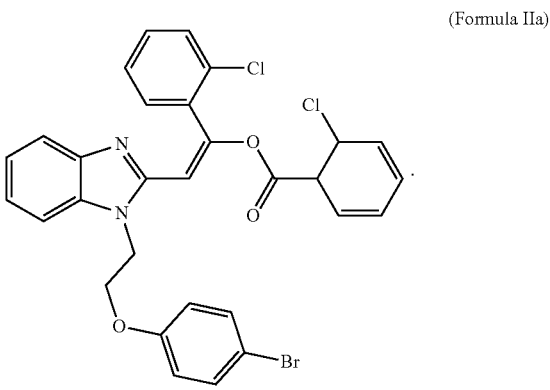 [SMILES: O=C(O/C(=C/c1nc2ccccc2n1CCOc1ccc(Br)cc1)c1ccccc1Cl)C1C=CC=CC1Cl]

(Formula IIa)

The compound of Formula IIa is sometimes referred to herein as CB-2.

In some embodiments, an MCT4 inhibitor is a compound, or a salt thereof, having the structure of formula III below:

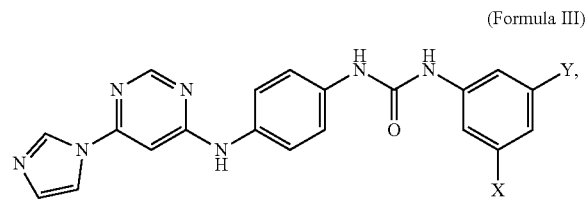

(Formula III)

wherein X and Y are independently selected from hydrogen, chlorine, fluorine, bromine and iodine. In some embodiments, X and Y of formula III are fluorine. In some embodiments, an MCT4 inhibitor is N-(3,5-difluorophenyl)-N'-(4-{[6-(1H-imidazol-1-yl)-4-pyrimidinyl]amino}phenyl)urea represented by formula IIIa below:

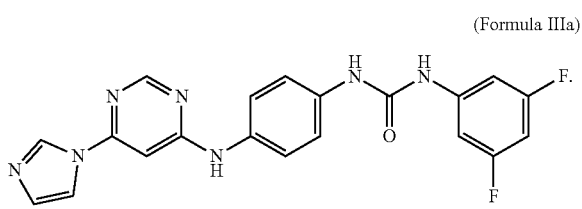 [SMILES: O=C(Nc1ccc(Nc2cc(-n3ccnc3)ncn2)cc1)Nc1cc(F)cc(F)c1]
(Formula IIIa)

The compound of Formula IIIa is sometimes referred to herein as CB-3.

In some embodiments, an MCT4 inhibitor is a compound disclosed herein that binds specifically to MCT4. In certain embodiments, an MCT4 inhibitor is a compound that inhibits, blocks, ameliorates, or suppresses MCT4 activity. Accordingly, in certain embodiments, an MCT4 inhibitor is a compound disclosed herein that inhibits, blocks, ameliorates, or suppresses MCT4 mediated transport of a monocarboxylate across a cell membrane. Non-limiting examples of a monocarboxylate are selected from lactate, pyruvate, branched-chain oxo acids derived from leucine, valine and isoleucine, acetoacetate, beta-hydroxybutyrate and acetate.

In certain embodiments, an MCT4 inhibitor is a compound disclosed herein that inhibits, blocks, ameliorates, or suppresses the viability, metastasis, or growth of a cancer. In certain embodiments, an MCT4 inhibitor is a compound disclosed herein that induces death, apoptosis, necrosis or cytotoxicity of a cancer (e.g., a cancer cell).

Any suitable method can be used to make or synthesize an MCT4 inhibitor compound disclosed herein. Methods of making, synthesizing, and modifying small compounds such as the MCT4 inhibitors described herein are described in "Organic Synthesis", Michael B. Smith, Second Edition, Copyright 2002, McGraw-Hill Higher Education; "Greene's Protective Groups in Organic Synthesis", Peter G. M. Wuts, Fifth Edition, Copyright 2014, John Wiley and Sons Inc.; and "The Organic Chemistry of Drug Synthesis", Vol. 7, Daniel Lednicer, Copyright 2008, John Wiley and Sons Inc.

Subjects

The term "subject" refers to animals, typically mammalian animals. In some embodiments a subject is a mammal. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a primate. In some embodiments a subject is a human. A mammal can be any age or at any stage of development (e.g., an adult, teen, child, infant, or a mammal in utero). A mammal can be male or female. In certain embodiments a mammal can be an animal disease model, for example, animal models used for the study of cancer.

In certain embodiments a subject has or is suspected of having a cancer. In certain embodiments a subject is at risk of developing a cancer. Subjects at risk of developing a cancer can be subjects in high risk groups who can be identified by a medical professional. Non-limiting examples of subjects at risk of cancer include chronic smokers, overweight individuals, human subjects over the age of 60, subjects with a family history of cancer, subjects having certain gene mutations that are associated with certain cancers, subjects infected with, or previously infected with certain viruses associated with the development of certain cancers, subjects exposed to known carcinogens, subjects exposed to excessive radiation (e.g., UV radiation, alpha, beta, or gamma radiation), subjects having chronic inflammation, the like, or combinations thereof. In certain embodiments a subject is at risk of developing a cancer is a cancer survivor, or a subject who previously had a cancer and is at risk of re-occurrence of the cancer. In some embodiments a subject or mammal is "at risk" of cancer metastasis. Certain cancers are known to be metastatic or have a high probability of metastasis depending on the cancer type, stage, tissue or origin, and/or age, sex or health condition of a subject. A subject at risk can be readily identified by a medical professional (e.g., a doctor, or an oncologists).

Methods of Treatment

In some embodiments, a method described herein comprises a method of treating a cancer in a subject that has, or is suspected of having, a cancer. In some embodiments, a method of treating a cancer comprises a method of inhibiting, blocking, ameliorating, reducing or suppressing growth or viability of a cancer in a subject. In some embodiments, a method of treating a cancer comprises a inhibiting, blocking, ameliorating, reducing or suppressing metastasis of a cancer in a subject. In certain embodiments, a method of treating a cancer in a subject comprises an attempt to inhibit, block, ameliorate, reduce or suppress growth, viability or metastasis of a cancer in a subject, with a reasonable expectation of success.

In certain embodiments, a method of treating a cancer comprises administering a therapeutically effective amount of an MCT4 inhibitor or composition described herein to a subject in need thereof. A subject in need can be a subject who has a cancer, is suspected of having a cancer or is at risk of having a cancer.

In certain embodiments, a method of treating a cancer comprises administering a therapeutically effective amount of an MCT4 inhibitor to a subject in need thereof, in combination with administering a therapeutically effective amount of another anti-cancer therapy. In certain embodiments, a method of treating a cancer comprises administering a therapeutically effective amount of an MCT4 inhibitor to a subject in need thereof, in combination with a therapeutically effective amount of a chemotherapy. In some embodiments, administering a chemotherapy comprises administering a therapeutically effective amount of a chemotherapeutic agent. In some embodiments, administering a chemotherapy comprises administering a therapeutically effective amount of a radiation therapy or radiation treatment.

In some embodiments, a method of treating a cancer comprises administering a therapeutically effective amount of an MCT4 inhibitor to a subject in need thereof, in combination with a therapeutically effective amount of metformin. An MCT4 inhibitor and metformin can be administered at the same time, or at different times.

Cancers & Metastasis

A composition, pharmaceutical composition or MCT4 inhibitor disclosed herein can be used to treat a neoplastic order or cancer. In some embodiments, a method disclosed herein comprises a method of treating a cancer in a subject who has, or is suspected of having, a neoplastic disorder or cancer. Non-limiting examples of a neoplastic disorder or cancer that can be treated by a method herein includes a carcinoma, sarcoma, neuro neoplasia, lymphoma, myeloma, leukemia, melanoma, mesothelioma, solid or soft tissue tumors, and secondary cancers (e.g., derived from a primary site)). Non-limiting examples of a carcinoma include respiratory system carcinomas, gastrointestinal system carcinomas, genitourinary system carcinomas, testicular carcinomas, prostatic carcinomas, endocrine system carcinomas, basal cell carcinoma of the skin, carcinoma of unknown primary, cholangiocarcinoma, ductal carcinoma in situ (DCIS), merkel cell carcinoma, lung carcinoma, thymoma and thymic carcinoma, midline tract carcinoma, lung small cell carcinoma, thyroid carcinoma, liver hepatocellular carcinoma, squamous cell carcinoma, head and neck squamous carcinoma, breast carcinoma, epithelial carcinoma, adrenocortical carcinoma, ovarian surface epithelial carcinoma, and the like, further including carcinomas of the uterus, cervix, colon, pancreas, kidney, esophagus, stomach and ovary. Non-limiting examples of a sarcoma include Ewing sarcoma, lymphosarcoma, liposarcoma, osteosarcoma, soft tissue sarcoma, Kaposi sarcoma, rhabdomyosarcoma, uterine sarcoma, chondrosarcoma, leiomyosarcoma, fibrosarcoma and the like. Non-limiting examples of a neuro neoplasia include glioma, glioblastoma, meningioma, neuroblastoma, retinoblastoma, astrocytoma, oligodendrocytoma and the like. Non-limiting examples of lymphomas, myelomas, and leukemias include acute and chronic lymphoblastic leukemia, myeloblastic leukemia, multiple myeloma, poorly differentiated acute leukemias (e.g., erythroblastic leukemia and acute megakaryoblastic leukemia), acute promyeloid leukemia (APML), acute myelogenous leukemia (AML), chronic myelogenous leukemia (CML), acute lymphoblastic leukemia (ALL), which includes B-lineage ALL and T-lineage ALL, chronic lymphocytic leukemia (CLL), prolymphocytic leukemia (PLL), hairy cell leukemia (HLL), Waldenstrom's macroglobulinemia (WM), non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Non-limiting examples of soft or solid tissue tumors include visceral tumors, seminomas, hepatomas, and other tumors of the breast, liver, lung, pancreas, uterus, ovary, testicle, head, neck, eye, brain, mouth, pharynx, vocal cord, ear, nose, esophagus, stomach, intestine, colon, adrenal, kidney, bone, bladder, urethra, carcinomas, lung, muscle, skin, feet, hands, and soft tissue.

In some embodiments, a cancer that can be treated by a method herein is a cancer that expresses MCT4. Accordingly, a cancer can be tested using a suitable method to determine if the cancer, or cells thereof, express MCT4 on their cell surface. A cancer, or cancer cell that expresses MCT4 on the cell surface of said cancer or cancer cell, is a cancer that can be treated with an MCT4 inhibitor disclosed herein.

Pharmaceutical Compositions, Administration and Dosing

In some embodiments, a composition comprises an MCT4 inhibitor. In some embodiments, a composition comprises an MCT4 inhibitor and one or more pharmaceutical excipients, diluents and/or carriers. In certain embodiments, a composition described herein is a pharmaceutical composition suitable for administration to a human subject. In certain embodiments, a pharmaceutical composition comprises an MCT4 inhibitor and one or more pharmaceutical excipients, diluents and/or carriers.

In some embodiments, a pharmaceutical composition is delivered to a subject or cancer cell via one or more delivery systems depending on the indication, disease state, severity, clinical utility and other relevant parameters that may impact the desired efficacy of a treatment using one or more MCT4 inhibitors described herein.

The exact formulation and/or route of administration of an MCT4 inhibitor (e.g., one or more MCT4 inhibitors) or a composition for use according to the methods of the invention described herein can be chosen by a physician in view of a patient's condition. See e.g., Fingl et al. 1975, in "The Pharmacological Basis of Therapeutics," Ch. 1 p. 1; which is incorporated herein by reference in its entirety. Any suitable route of administration can be used for administration of a composition (e.g., a pharmaceutical composition) or an MCT4 inhibitor described herein. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intraarticular, into a joint space, intracardiac (into the heart), intracavernous injection, intralesional (into a skin lesion), intraosseous infusion (into the bone marrow), intrathecal (into the spinal canal), intrauterine, intravaginal, intratumoral, intravesical infusion, intravitreal), the like or combinations thereof.

In some embodiments one or more MCT4 inhibitors or a composition described herein is provided to a subject. A composition that is provided to a subject is sometimes provided to a subject for self-administration or for administration to a subject by another (e.g., a non-medical professional). For example a composition described herein can be provided with an instruction written by a medical practitioner that authorizes a patient to be provided a composition or treatment described herein (e.g., a prescription). In another example, a composition can be provided to a subject wherein the subject self-administers a composition orally, intravenously, topically or by way of an inhaler, for example.

One or more MCT4 inhibitors and compositions (e.g., compositions comprising a one or more MCT4 inhibitors) can be formulated to be compatible with a particular route of administration or use. Compositions for parenteral, intradermal, or subcutaneous administration can include a sterile diluent, such as water, saline solution, fixed oils, polyethylene glycols, glycerin, propylene glycol or other synthetic, aqueous or organic solvents. A pharmaceutical composition may contain one or more preservatives to prevent microorganism growth (e.g., antibacterial agents such as benzyl alcohol or methyl parabens, antifungal agents and the like); antioxidants such as ascorbic acid or sodium bisulfite; chelating agents such as EDTA; buffers such as acetates, citrates or phosphates and agents for the adjustment of tonicity such as sodium chloride or dextrose. Antibacterial and antifungal agents include, for example, parabens, chlorobutanol, phenol, ascorbic acid and thimerosal.

Compositions for injection include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. In some embodiments, a pharmaceutical composition includes an agent that delays absorption, for example, aluminum monostearate and gelatin which can prolong absorption of injectable compositions. In some embodiments, a pharmaceutical composition comprises polysorbate 20 or polysorbate 80, for example, up to 1%. Other non-limiting additives include histidine HCl, and α,α-trehalose dehydrate.

In some embodiments, one can administer compositions for use according to the methods of the invention in a local rather than systemic manner, for example, via direct application to the skin, mucous membrane or region of interest for treating, including using a depot or sustained release formulation. In some embodiments, a pharmaceutical composition comprising one or more MCT4 inhibitors described herein can be formulated, for example, as a topical formulation. The topical formulation may include, for example, a formulation such as a gel formulation, a cream formulation, a lotion formulation, a paste formulation, an ointment formulation, an oil formulation, and a foam formulation. The composition further may include, for example, an absorption emollient. In certain embodiments, a pharmaceutical composition comprising one or more MCT4 inhibitors described herein can be formulated, for example, for administration to the upper respiratory track/bronchi in a mammal in need thereof, for example, by contacting at least part of the upper respiratory tract/bronchi of a mammal with a therapeutically effective amount of a composition as disclosed above or elsewhere herein. The composition can be, for example, formulated as an aerosol formulation, including formulated for use in a nebulizer or an inhaler. The compositions may therefore include, for example, one or more of dichlorodifluoromethane, trichlorofluoromethane, dichlorotetrafluoroethane, carbon dioxide, and the like.

In some embodiments, active ingredients (e.g., one or more MCT4 inhibitors) can be administered alone or formulated as a composition (e.g., a pharmaceutical composition). In other embodiments, a one or more MCT4 inhibitors can be administered in combination with one or more additional materials (e.g., one or more chemotherapeutic agents or cytokines), for example, as two separate compositions or as a single composition where the additional material(s) is (are) mixed or formulated together with a one or more MCT4 inhibitors. For example, without being limited thereto, one or more MCT4 inhibitors can be formulated with additional active ingredients. For example, one or more MCT4 inhibitors can be formulated with Metformin. Accordingly, in certain embodiments, a composition for use in treating cancer comprises an MCT4 inhibitor and Metformin.

A pharmaceutical composition can be manufactured by any suitable manner, including, e.g., by means of conventional mixing, dissolving, granulating, dragee-making, levigating, emulsifying, encapsulating, entrapping or tableting processes.

Pharmaceutical compositions comprising an MCT4 inhibitor described herein can be formulated in any suitable manner using one or more pharmaceutically acceptable excipients non-limiting examples of which include carriers, solvents, salts, additives, preservatives, and/or auxiliaries. Proper formulation can depend upon the route of administration chosen. In particular, a pharmaceutical compositions can comprise any suitable carrier, formulation, or ingredient, the like or combinations thereof as listed in "Remington: The Science And Practice Of Pharmacy" Mack Publishing Co., Easton, Pa., 19$^{th}$ Edition, (1995), or "Remington: The Science And Practice Of Pharmacy", Pharmaceutical Press, Easton, Pa., 22$^{nd}$ Edition, (2013). The various materials listed herein, alone or in combination, can be incorporated into or used with the materials described in Remington's.

Any suitable techniques, carriers, and excipients can be used, including those understood in the art; e.g., in Remington's Pharmaceutical Sciences, above.

In some embodiments, a carrier includes one or more chemical compounds that facilitate the incorporation of an active ingredient (e.g., one or more MCT4 inhibitors) into cells or tissues. For example dimethyl sulfoxide (DMSO) is a commonly utilized carrier as it facilitates the uptake of many compounds and peptides into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

In certain embodiments, a pharmaceutical composition comprises hydrophobic excipients, additives, or other hydrophobic components. A pharmaceutical carrier for certain hydrophobic peptides can be a co-solvent system comprising benzyl alcohol, a nonpolar surfactant, a water-miscible organic polymer, and an aqueous phase. A common co-solvent system contemplated for use herein is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of POLYSORBATE 80™; the fraction size of polyethylene glycol can be varied; other biocompatible polymers can replace polyethylene glycol, e.g., polyvinyl pyrrolidone; and other sugars or polysaccharides can substitute for dextrose.

Alternatively or additionally, other carriers can be employed, if required. Liposomes and emulsions are well known examples of delivery vehicles or carriers for hydrophobic drugs and drug compositions. Additionally, the one or more MCT4 inhibitors described herein can be delivered using a sustained-release system, such as semipermeable matrices of solid hydrophobic polymers containing the therapeutic agent. The pharmaceutical compositions described herein can be administered to a patient per se, or in pharmaceutical compositions where they are mixed with other active ingredients, as in combination therapy, or suitable carriers or excipient(s). The compounds and compositions can be formulated with salts or excipients, such as for example, sodium or meglumine. Techniques for formulation and administration of the one or more MCT4 inhibitors of the instant application can be found in "Remington's Pharmaceutical Sciences," Mack Publishing Co., Easton, Pa., 18th edition, 1990.

Furthermore, the compounds and compositions used herein can be stable over an extended period of time, for example on the order of months or years. Compositions described herein, in some embodiments, may comprise a preservative. The preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). The preservative can comprise an alkyl-mercury salt of thiosalicylic acid, such as thiomersal, phenylmercuric nitrate, phenylmercuric acetate or phenylmercuric borate. The preservative can comprise parabens, such as methylparaben or propylparaben. The preservative can comprise an alcohol, such as chlorobutanol, benzyl alcohol or phenyl ethyl alcohol. The preservative can comprise a biguanide derivative, such as chlorohexidine or polyhexamethylene biguanide. The preservative can comprise sodium perborate, imidazolidinyl urea, and/or sorbic acid. The preservative can comprise stabilized oxychloro complexes, such as known and commercially available under the trade name PURITE®). The preservative can comprise polyglycol-polyamine condensation resins, such as known and commercially available under the trade name POLYQUART® from Henkel KGaA. The preservative can comprise stabilized hydrogen peroxide generated from a source of hydrogen peroxide for providing an effective trace amount of resultant hydrogen peroxide, such as sodium perborate tetrahydrate. The preservative can be benzalkonium chloride.

The preservative can enable a composition to be used on multiple occasions. The preservative can reduce the effects of one or more of acid exposure, base exposure, air exposure, heat, and light on the active ingredient. The compounds and pharmaceutical compositions described herein can include any suitable buffers, such as for example, sodium citrate buffer and/or sequestering agents, such as edetate disodium sequestering agent. Ingredients, such as meglumine, may be added to adjust the pH of a composition or compound described herein. Compounds and compositions described herein may comprise sodium and/or iodine, such as organically bound iodine. Compositions and compounds used herein may be provided in a container in which the air is replaced by another substance, such as nitrogen.

Certain embodiments provide pharmaceutical compositions comprising one or more MCT4 inhibitors in an amount effective to achieve its intended purpose (e.g., a therapeutically effective amount). A "therapeutically effective amount" means an amount to prevent, treat, suppress, inhibit, reduce the severity of, delay the onset of, suppress or inhibit the growth or viability of a cancer, metastasis of a cancer or one or more symptoms associate with a cancer. A symptom can be a symptom already occurring or expected to occur. Determination of a therapeutically effective amount is well within the capability of those skilled in the art (e.g., a medical practitioner), especially in light of the detailed disclosure provided herein.

In some embodiments, a therapeutically effective amount is an amount needed for a significant quantity of a pharmaceutical composition (or MCT4 inhibitor therein) to contact a desired region or tissue where prevention or treatment of a cancer is desired.

A resulting effect of a treatment herein, in certain embodiments, is to inhibit, suppress, ameliorate or reduce the viability, metabolism, growth, size, amount or metastasis of a cancer. In some embodiments, the resulting effect of a treatment herein is to inhibit, suppress, ameliorate or reduce the frequency or severity of one or more symptoms associated with a cancer. The resulting effect of a treatment herein, in certain embodiments, is to inhibit, prevent, suppress, ameliorate or reduce the re-occurrence of a cancer in a subject. The overall beneficial effect of a treatment described herein can be determined by comparing the condition or disease state of a subject who received a treatment described herein to one or more individuals who have not received treatment, or to the same patient prior to treatment, or after cessation of, treatment. A treatment may be complete (no detectable symptoms or cancer) or partial, such that fewer symptoms or amounts of a cancer are observed than would likely occur absent treatment.

Compositions described herein can be administered at a suitable dose, e.g., at a suitable volume and concentration depending on the route of administration. Within certain embodiments of the invention, dosages of an active ingredient of an administered composition (e.g., an MCT4 inhibitor) can be from a concentration, for example, of 0.1 µg/kg to 500 mg/kg (e.g., amount of active ingredient/body weight of a subject), 0.1 µg/kg to 100 mg/kg, 0.1 ng/kg to 1 mg/kg, 0.1 ng/kg to 100 mg/kg, 0.001 mg/kg to 100 mg/kg, 0.001 mg/kg to 10 mg/kg, 0.001 mg/kg to 1 mg/kg, about 0.01 mg/kg to 100 mg/kg, about 0.01 mg/kg to about 50 mg/kg, about 0.1 mg/kg to about 500 mg/kg, about 0.1 mg/kg to about 250 mg/kg, about 0.1 mg/kg to about 100 mg/kg, or about 1 mg/kg to about 100 mg/kg. In certain embodiments a composition or one or more MCT4 inhibitors described herein can be administered at a concentration of at least 0.01 mg/kg, at least 0.1 mg/kg, at least 1 mg/kg, at least 10 mg/kg, at least 20 mg/kg, or at least 50 mg/kg. In certain embodiments a composition or one or more MCT4 inhibitors described herein is administered at a concentration of about 1 mg/kg, about 10 mg/kg, about 15 mg/kg, about 20 mg/kg, about 25 mg/kg, or about 30 mg/kg. The concentrations recited above can refer to the concentration of a single MCT4 inhibitor and can be adjusted accordingly when two or more MCT4 inhibitors are used. In certain embodiments a composition is administered to a concentration in a range of 0.1 mg /kg to 10 mg/kg body weight of a subject. Volumes suitable for intravenous administration are well known. For example, 0.1 ml-100 ml of a composition comprising an MCT4 inhibitor can be safely administered intravenously to an adult human subject.

In some embodiments, administering a therapeutically effective amount comprises administering a suitable dose of a pharmaceutical composition at a suitable frequency. For example, in certain embodiments, a therapeutically effective dose is administered on an as-needed basis, or on a regular interval, for example on a daily basis, twice daily, three times daily, or every other day. A composition comprising one or more MCT4 inhibitors can be administered for a period of time ranging from a single as needed administration to administration for 1 day to multiple years, or any value there between, (e.g., 1-90 days, 1-60 days, 1-30 days, etc.). The dosages described herein can be daily dosages or the dosage of an individual administration, for example, even if multiple administrations occur.

Kits

In some embodiments the compositions, formulations, combination products and materials described herein can be included as part of a kit, which kit can include one or more MCT4 inhibitors, metformin, a chemotherapeutic agent for combination treatments and products and other materials described herein. In some embodiments a kit comprises one or more MCT4 inhibitors, or a pharmaceutical composition comprising the same. In some embodiments a kit comprises one or more MCT4 inhibitors as described herein and a chemotherapeutic agent. In some embodiments a kit comprises one or more MCT4 inhibitors as described herein and metformin.

In certain embodiments, a kit comprises an amount of a lyophilized MCT4 inhibitor and a pharmaceutically acceptable diluent suitable for reconstitution of the MCT4 in a liquid form. In some embodiments, a kit includes a applicator (e.g., a syringe) for administering an MCT4 inhibitor.

In some embodiments a kit comprises an amount of an MCT4 suitable to treat a subject for 1 day to 1 year, 1 day to 180 days, 1 day to 120 days, 1 day to 90 days, 1 day to 60 days, 1 day to 30 days, or any day or number of days there between. In some embodiments, a kit comprises 1 ug to 10,000 mg of an MCT4 inhibitor described herein. In some embodiments, a kit comprises MCT4 formulated as a capsule or tablet, where the kit comprises 1 to 1000 capsules and/or tablets.

In some embodiments, a kit comprises suitable packaging materials. A kit optionally includes a label or packaging insert including a description of the components or instructions for use in vitro, in vivo, or ex vivo, of the components therein. Exemplary instructions include instructions for a method, treatment protocol or therapeutic regimen described herein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards. Labels or inserts can include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

Labels or inserts can include information on a condition, cancer, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Components of the kit can be enclosed within an individual container and all of the various containers can be within a single package. Invention kits can be designed for cold storage.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed.

EXAMPLES

Example 1

Homology Modeling of Human MCT4 Structure and Virtual Screening

The 3D model of the human MCT4 structure was generated using the I-TASSER On-line Server found at [URL: https://zhanglab.ccmb.med.umich.edu/I-TASSER/])(Zhang Y. (2008) *BMC Bioinformatics* 9:40). Virtual screening and docking were performed using Glide version 4.5 (Schrodinger Suite 2007) based on the human MCT4 structure model with default docking parameter settings (Friesner R A, et al. (2004) *J Med Chem* 47:1739-49). Hydrogen atoms and charges were added during a brief relaxation performed using the "Protein Preparation" module in Maestro with the "preparation and refinement" option, and a restrained partial minimization was terminated when the root-mean-square deviation (RMSD) reached a maximum value of 0.3 Å in order to relieve steric clashes of amino acid residues located within 20 Å from the residues of Trp20, Gln205, Thr349 and Asp439 that were defined as part of the binding site for the docking studies.

Seven compound libraries were virtually screened that included more than 5.5 million compounds for targeting the binding site of MTC4 defined by the structural modeling herein. All compounds were desalted, neutralized, and parameterized using the OPLS 2005 force field. Then, tautomers and ionization states expected to occur in the pH range of 5.0-9.0 were generated using the "ionize" module. In the docking process, standard-precision (SP) and extra-precision (XP) docking were respectively adopted to generate the minimized pose, and the Glide scoring function (G-Score) was used to select the final pose with the lowest energy conformation for each compound ligand. The compounds with the top ranked scores were further visually inspected and analyzed by experimental testing.

Cell Culture

Human cell lines MDA-MB-231 cells were obtained from ATCC (Rockville, Md.). These cells were authenticated by Laragen, Inc. (Culver City, Calif.), by short tandem repeat (STR) profiling, monitoring cell morphology and biological behavior, and tested to exclude mycoplasma contamination prior to use.

Viability/Cytotoxicity Assay

A viability/cytotoxicity assay was performed by culturing cells in 96-well plates. The following day the cells were treated with ½ serial dilutions of each compound or the solvent (DMSO) alone as a control. The amount of solvent was the same in all the conditions and each condition was tested in duplicate or triplicate. After 5 days incubation, the effect of the compounds on cell proliferation were determined by either MTT (3-(4,5-dimethylthiazol-2-yl)-2,5-diphenyltetrazolium bromide, Sigma-Aldrich, St. Louis, Mo.) or bioluminescence assay (Cell Titer Glo, Promega, Madison, Wis.). After incubation of the cells with MTT (1 mg/ml), the developed color was dissolved in DMSO and read by a plate reader. The bioluminescence assays were performed according to the manufacturer's recommendation. Growth inhibition rates were determined by comparing the read out for each compound dilution versus the control and from the growth inhibition curves from which the $IC_{50}$ values were calculated. Each assay was performed at least twice.

Lactate Secretion Assay

MDA-MB-231 cells were incubated with various candidate compounds (2.5 µM) for 48 hours followed by lactate secretion assay with a LACTATE-GLO™ Assay kit (Promega Corporation, Madison, Wis.) according to the manufacturer's protocol.

Western Blot and Immunoprecipitation

For MCT4 association with Biotin-CB-2, the cell lysate was incubated with three different Biotin-CB-2s, followed by streptavidin pull-down assay. The level of MCT4 associated with Biotin-CB-2s was analyzed through Western-blotting analysis. Densitometry was performed using Scion Image software (Scion Corp., Frederick, Md.).

Results

Discovery of Novel MCT4 Inhibitors by Structure-Based Virtual Screening

Lactic acid export from glycolytic cells is predominantly mediated by MCT4. Though MCT4 is absent from most normal tissues, MCT4 expression is highly upregulated, and correlates with poor survival, in many cancer indications, including breast cancer (e.g., triple-negative breast cancer), colorectal cancer, glioma, head and neck cancer, prostate cancer, liver cancer, and kidney cancer. Our data demonstrated that metabolic reprogramming, including promotion of glycolysis-mediated lactate production and inhibition of MCT4-mediated lactic acid export can be an effective strategy for treating diabetes-associated breast cancer and other cancers. Unfortunately, prior to this paper, no potent and selective MCT4 inhibitors have been described. Some moderate to weak MCT4 inhibitors are known (e.g., phloretin and α-CN-4-OH-cinnamate); however, these compounds promiscuously inhibit a number of other transporters, including MCT1.

It was the aim of this study to identify novel MCT4 inhibitors by structure-based virtual screening, which has become an integral part of this drug discovery process. After generating the 3D model of human MCT4 structure using the I-TASSER on-line server, potential compound candidates were identified and screened to determined their activity against MCT4. Two hundred thirty seven potential MCT4 inhibitors were identified using docking-based virtual screening. These compounds were evaluated for their ability to inhibit lactate secretion (by LACTATE-GLO™ Assay) and to inhibit cancer cell viability (evaluated by Cell Viability Screening). A representative example of the screening process is shown in FIG. 1. Certain representative compounds such as CB-2 (FIG. 2A), showed a significant inhibitory effect on lactate secretion and striking cytotoxic activity against MDA-MB-231 cells, which was higher than that of the diclofenac control that was previously reported to inhibit MCT4. This data suggests that the MCT4 inhibitors identified herein can be used to treat cancer.

CB-2 Targets the MCT4 Molecule

Figure 2B:
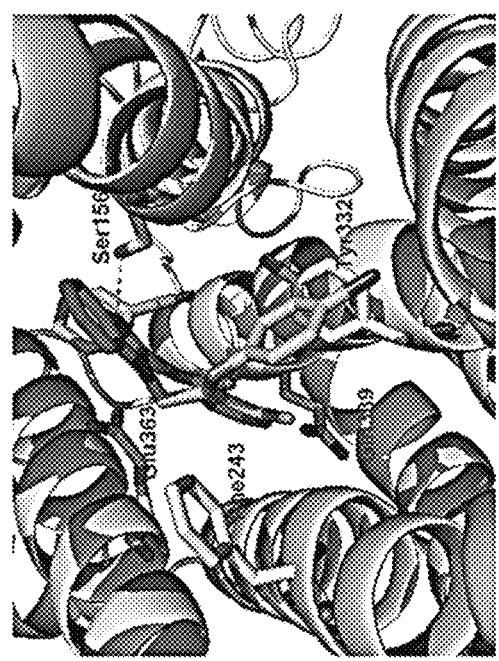
FIG. 2B shows a predicted binding mode for CB-2 to a portion of MCT4 revealing that CB-2 might bind to a pocket of MCT4 composed of Ser156, Phe243, Tyr332, Gln339 and Glu363 indicating that the side chain of Ser156 forms important hydrogen bonds with CB-2.
Figure 2C:
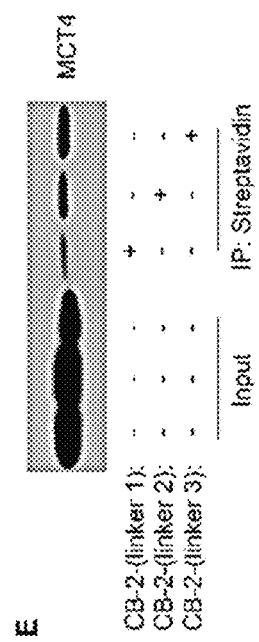
FIG. 2C shows the chemical structures of biotinylated CB-2 with three different linker positions.
Figure 2D:
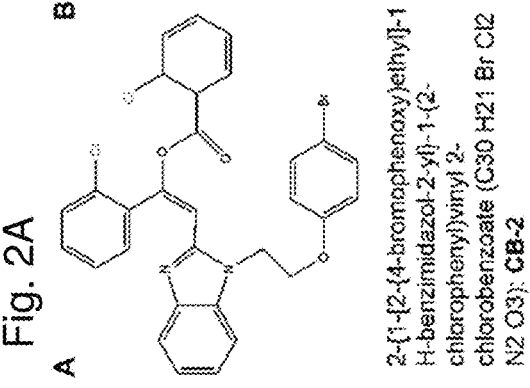
FIG. 2D shows IC50 curves for MDA-MB-231 cells treated with three different Biotin-CB-2 compounds. Percentage of cell growth inhibition (y-axis) is plotted against the treatment concentrations of CB-2 (x-axis).
Figure 2E:
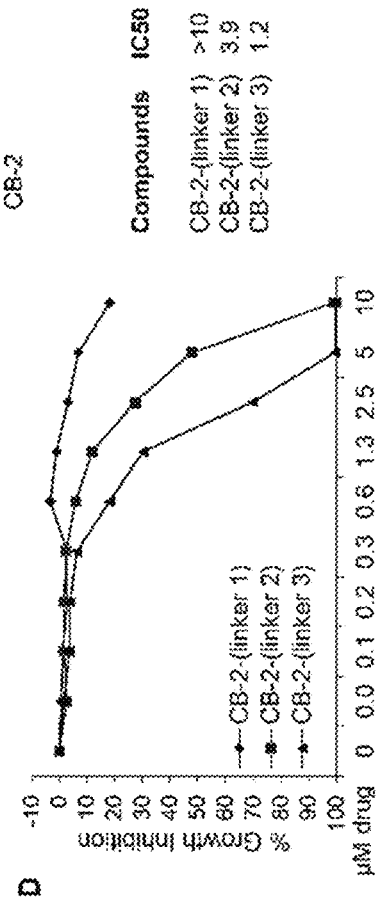
FIG. 2E shows a Western blot (Top panel) showing that MCT4 co-precipitates with Biotin-CB-2. Briefly, cell lysates were incubated with three different Biotin-CB-2s (linker 1, linker 2 and linker 3), followed by streptavidin pull down. The level of MCT4 associated with Biotin-CB-2s was analyzed through Western-blotting analysis.

To provide insights into CB-2 interactions with MCT4, docking simulation was performed for binding modes of CB-2 to the MCT4 Molecule. The predicted binding modes revealed that CB-2 might bind to a pocket of MCT4 composed by Ser156, Phe243, Tyr332, Gln339 and Glu363. The side chain of Ser156 forms important hydrogen bonds with CB-2 (FIG. 2B). To identify the direct target(s) of CB-2, we employed a pull-down approach using biotinylated CB-2 analogs. A biotin moiety connected to a linker was attached to CB-2 at three different positions of a benzene ring, forming three CB-2 analogs (Biotin-CB-2-(linker 1-3)) (FIG. 2C). A growth inhibition assay was carried out to check whether CB-2 remained active following biotinylation. Biotin-CB-2-linker 2 and 3 showed significant cytotoxicity against MDA-MB-231 cells with $IC_{50}$ values of 3.9 µM and 1.2 µM, respectively, whereas, Biotin-CB-2-linker 1 did not show marked inhibitory effects (FIG. 2D). Based on these results, a pull-down assay was conducted using Biotin-CB-2-(linker 1-3) to confirm binding to MCT4. The specific enrichment of MCT4 in the Biotin-CB-2 fractions was confirmed by Western blot analysis (FIG. 2E).

Docking Simulation for Binding Modes of CB-1 & CB-3 to the MCT4 Domain

Figure 3A:
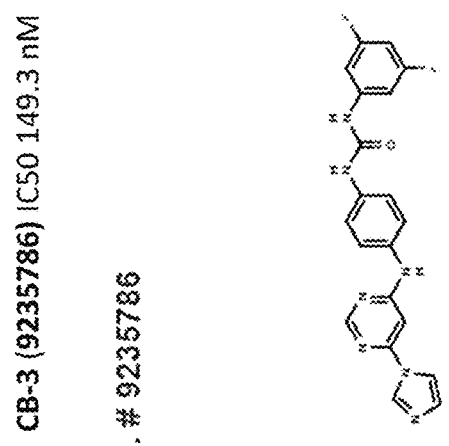
FIG. 3A shows the chemical structure of CB-3.
Figure 3B:
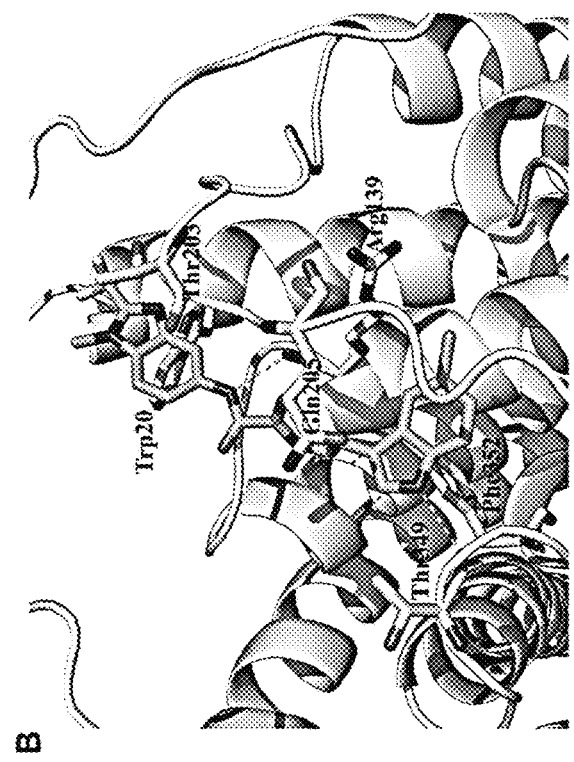
FIG. 3B shows a predicted binding mode for CB-3 to a portion of MCT4 revealing that CB-3 might bind to a pocket of MCT4 composed of Trp20, Arg139, Thr203, Gln205, Thr349 and Phe352, indicating that CB-3 forms important hydrogen bonds with the side chains of Arg139 and Thr349. Figures were generated by PyMol.
Figure 4A:
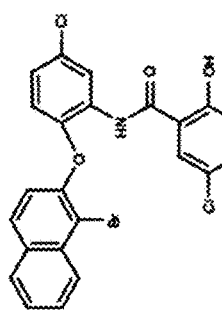
FIG. 4A shows the chemical structure of CB-1.
Figure 4B:
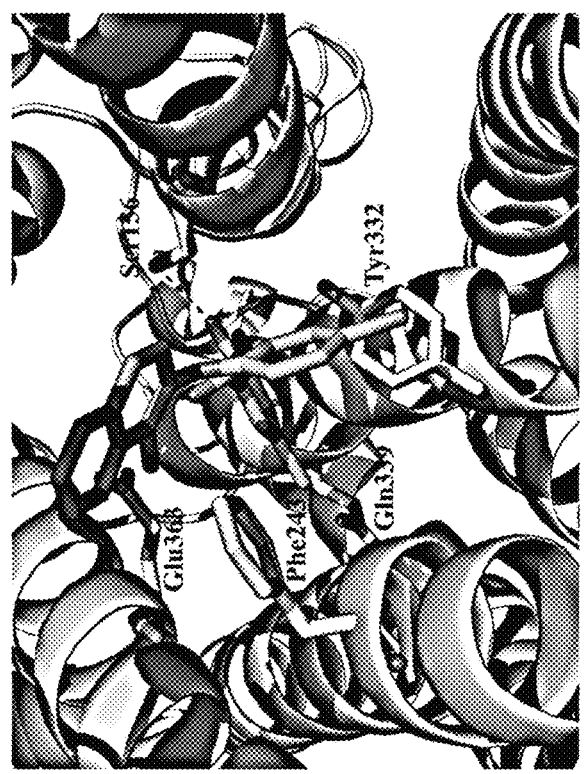
FIG. 4B shows a predicted binding mode for CB-1 to a portion of MCT4 revealing that CB-1 might bind to a pocket of MCT4 composed of Ser156, Phe243, Tyr332, Gln339 and Glu363. The side chain of Ser156 appears to form important hydrogen bonds with CB-1. Figures were generated by PyMol.

Docking simulation was also performed for binding modes of CB-1 and CB-3 to the MCT4 molecule. The predicted binding modes revealed that CB-3 may bind to a pocket of MCT4 composed of Trp20, Arg139, Thr203, Gln205, Thr349 and Phe352, and forms important hydrogen bonds with the main chains of Arg139 and Thr349 (FIG. 3). Further, the predicted binding modes of CB-1 and CB-2 show binding to the same pocket of MCT4 composed of Ser156, Phe243, Tyr332, Gln339 and Glu363, where the side chain of Ser156 forms important hydrogen bonds with these compounds (FIG. 4).

Figure 5:
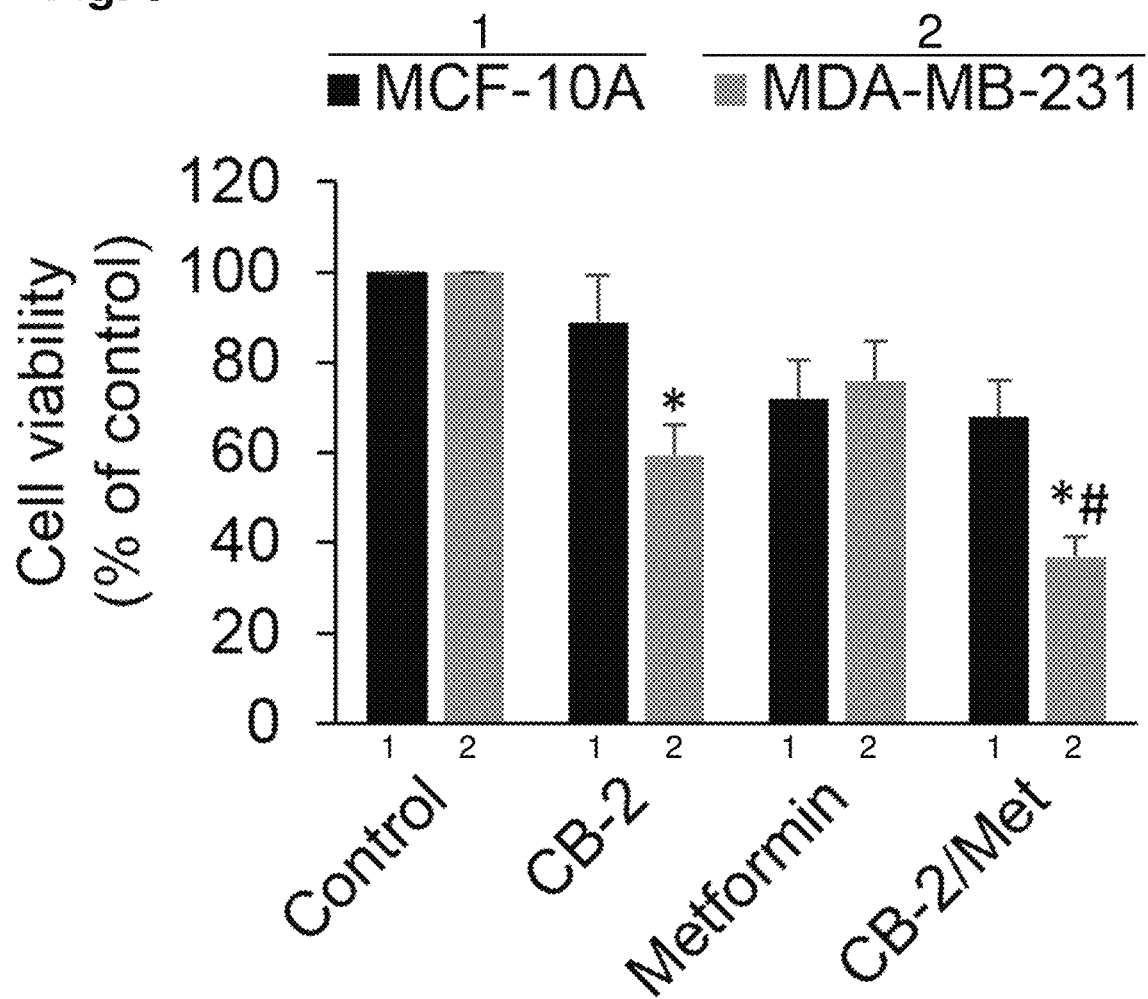
FIG. 5 shows the viability of MCF-10A and breast cancer MDA-MB-231 cells that were treated with CB-2 (5 µM), metformin (Met, 0.75 mM) or CB-2+Metformin for 3 days. After 3 days of incubation, the media was removed and the growth inhibition was detected by MTT assay. *P<0.05 vs. MCF-10A; #P<0.05 vs. metformin alone.

The combination of Metformin and CB-2 Exerts a Deleterious Effect on Breast Cancer Cell Viability Metformin, is a well-tolerated oral agent that is often used as a first-line treatment for type 2 diabetes. Due to its purported effects on oxidative phosphorylation, a combination treatment using both CB-2 and metformin was tested. The combination of the two compounds together demonstrated a enhanced cytotoxic effect on cancer cells compared to treatment of cells with metformin or CB-2 alone (FIG. 5). The results of the combination treatment showed a 63% inhibition of cell viability in MDA-MB-231 breast cancer cells. In contrast, a moderate effect on cell viability was observed in normal MCF-10A human mammary epithelial cells.

Figure 6:
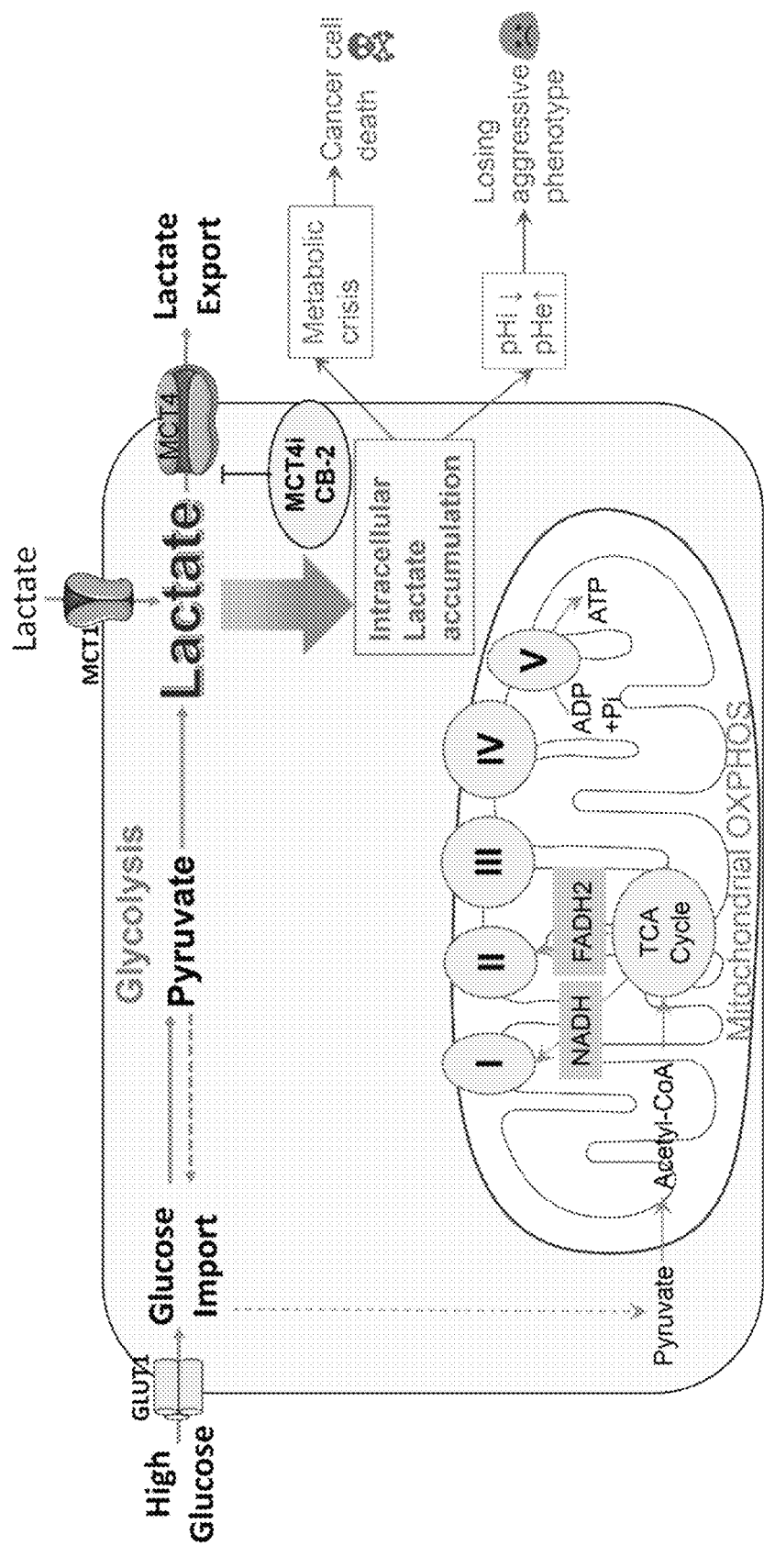
FIG. 6 shows a schematic illustrating a potential mechanism of CB-2 anti-tumor effects.
Figure 7:
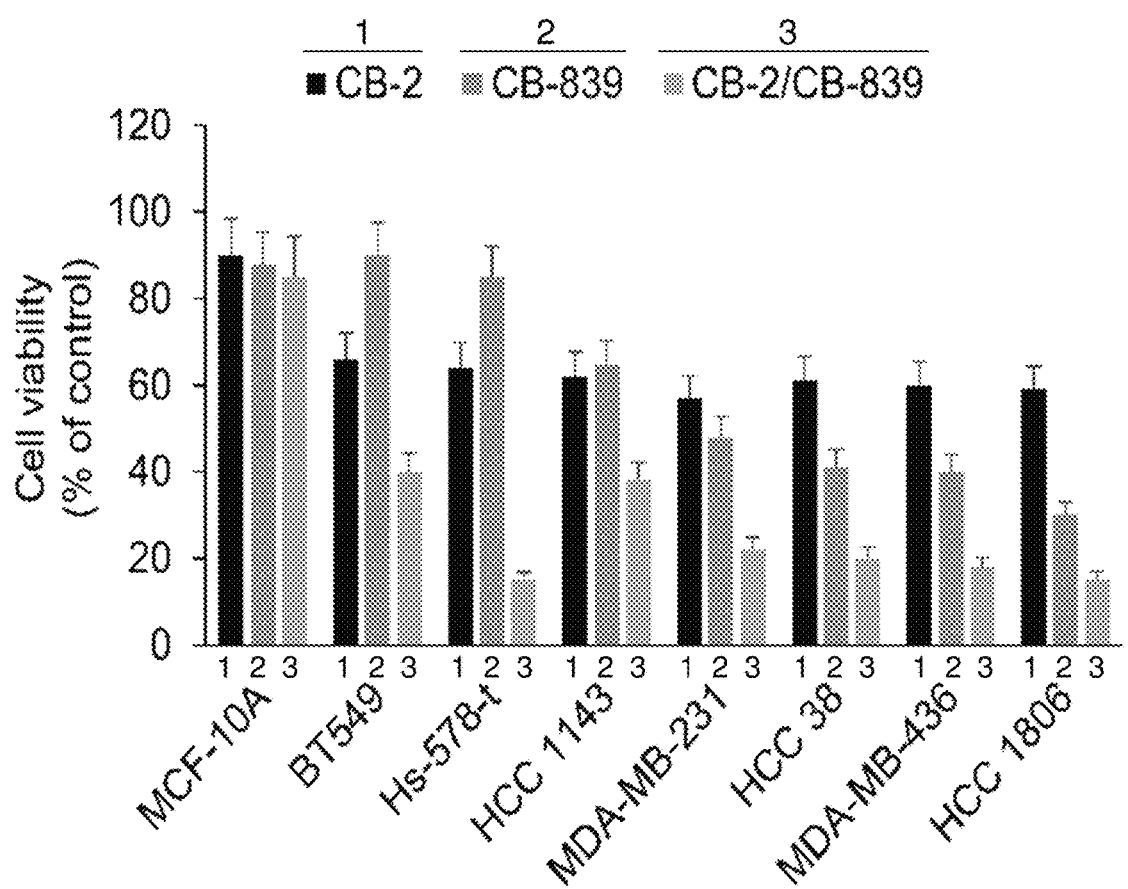
FIG. 7 shows a bar graph of cell viability (y-axis) of the indicated cancer cell lines (x-axis) after treatment with CB-2, CB-839, or both CB-2 and CB-839. MCF-10A and p53 mutant TNBC cells were treated with CB-2 (5 µM), CB-839 (2 µM) or CB-2+CB-839 for 3 days. After 3 days of incubation, the media was removed and the growth inhibition was detected by MTT assay. The results of FIG. 7 illustrate a potential mechanism of CB-2 anti-tumor effects. Combined use of CB-2 and CB-839 is synergistic in the treatment of p53 mutant TNBC cells.
Figure 8C:
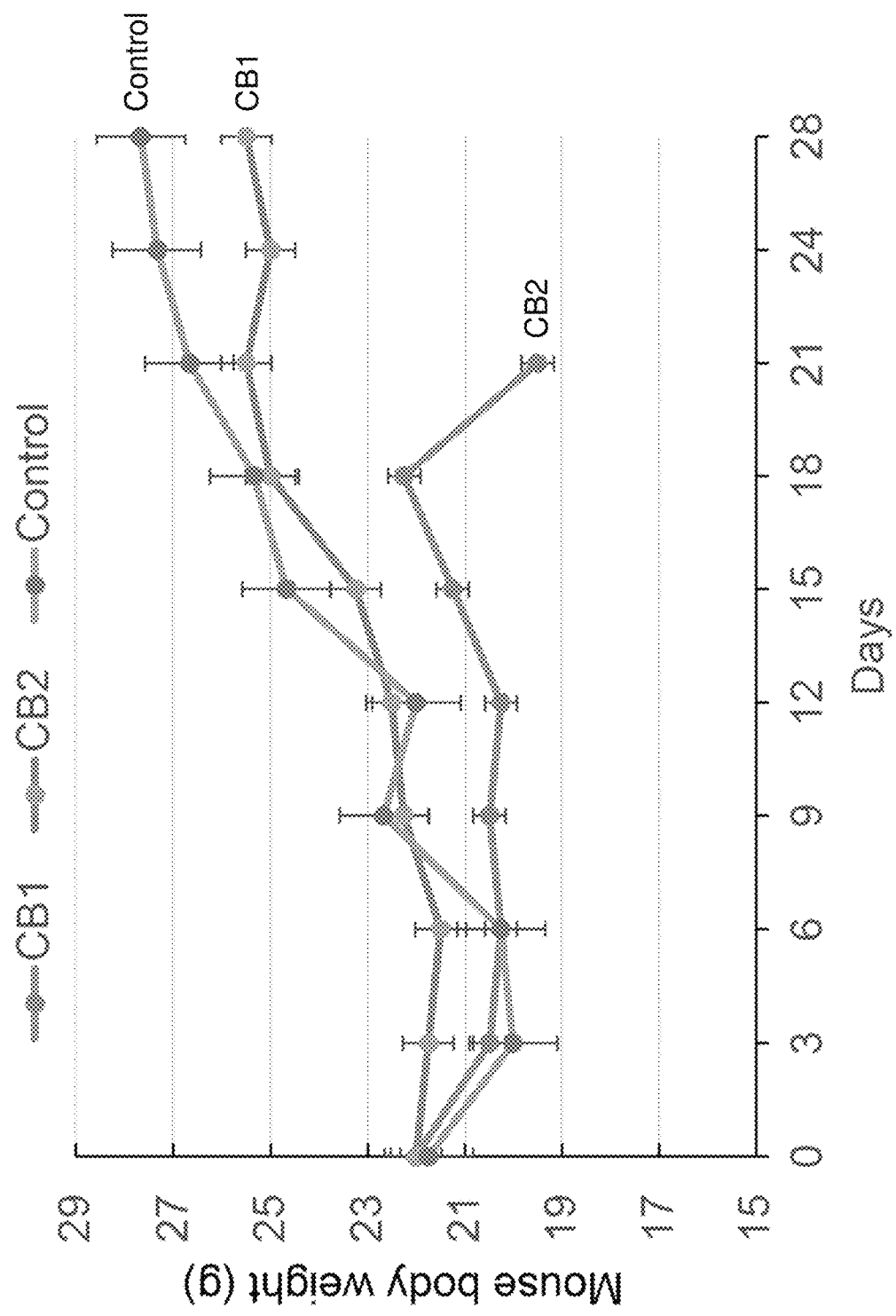
Figure 9C:
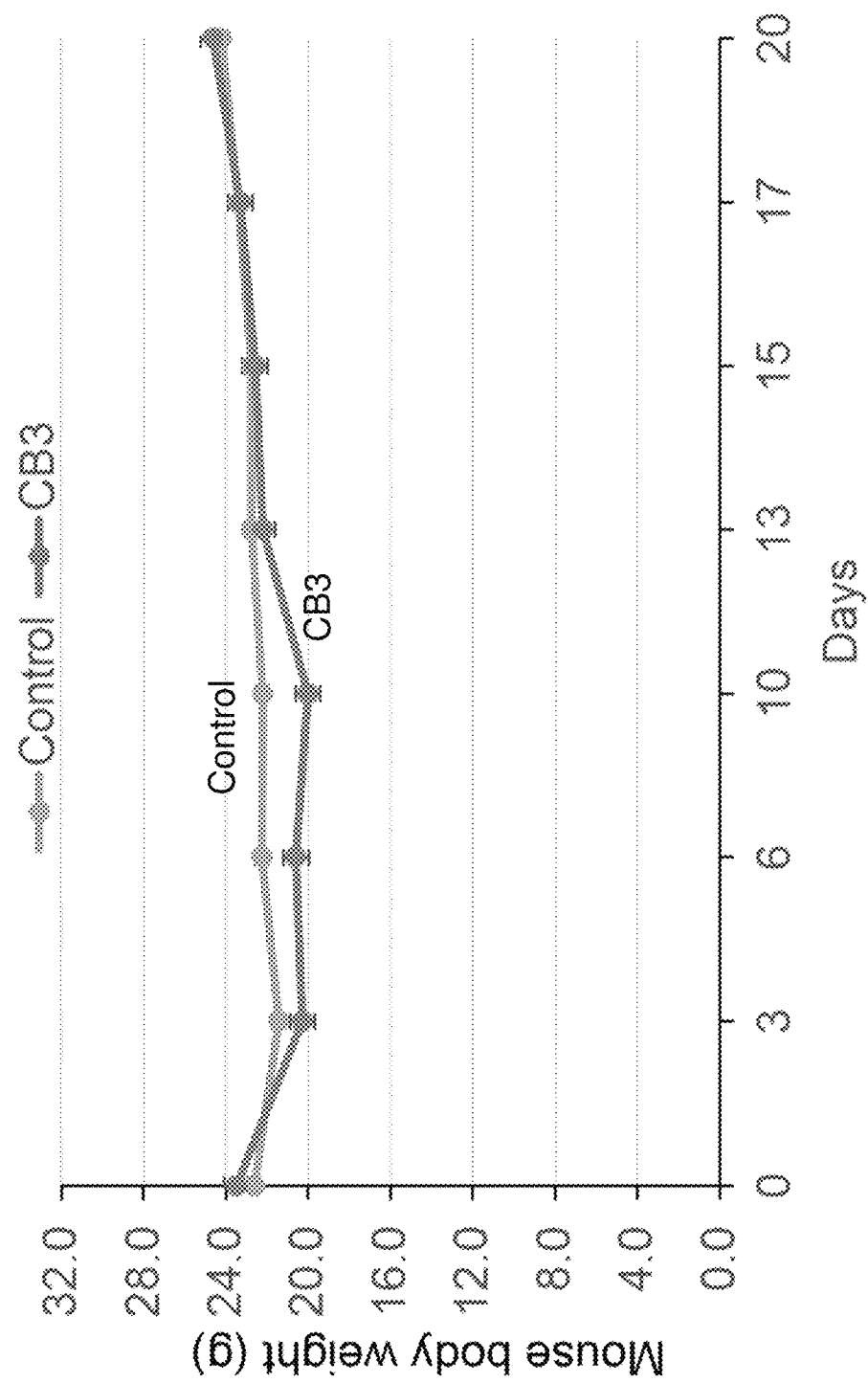

The synergistic effects observed for the combination treatment of Metformin and CB-2 might be explained because CB-2 blocks lactate export by inhibiting MCT4 function. Further, disrupting MCT4 function may lead to an accumulation of intracellular lactate and a decrease in intracellular pH (e.g., see FIG. 6) which may rapidly damage a cell thereby inducing necrosis, apoptosis or growth arrest. The application of metformin may increase glycolysis thereby increasing the buildup of intracellular lactate thereby accelerating the effects of the MCT4 inhibitor. Overall, the combined treatment of CB-2 and metformin can be used to treat high glycolytic rate/MCT4-expressing malignancies.

The Combination of CB-2 and Glutaminase 1 (GLS1) Inhibitor CB-839 Exerted Synergistic Inhibitory Effects on the Growth of p53 Mutant Basal TNBCs The consumption of glutamine is increase in most tumors, particularly p53 mutant basal triple negative breast cancer (TNBC) cells. Glutamine is converted to glutamate and ammonia by the catalytic activity of glutaminase (GLS) enzyme. During tumorigenesis, lactate produced by glucose metabolism increases, while tricarboxylic acid (TCA) oxidative phosphorylation of glucose is reduced. As glucose metabolism changes, glutamine metabolism is upregulated to compensate for deficiencies in energy metabolism and macromolecules required for cell proliferation and growth. There are two different isoforms of GLS, GLS1 and GLS2, which possess discrete tissue distribution and molecular regulation. GLS1 accounts for the majority of glutaminase activity in some human cancer cells and is upregulated in cells with augmented rates of proliferation. GLS2 was confirmed to be a p53 target gene in both non-tumor and tumor cells. In p53 mutant basal TNBC cells, GLS1 is highly expressed.

A combination of an MCT4 inhibitor CB-2 and a GLS1 inhibitor CB-839 (Calithera Bioscience Company) were used to reengineer cancer metabolism. This innovation extends the usage and effect of both GLS inhibitors and MCT4 inhibitors in breast cancer patients. One rationale for using the MCT4 inhibitor CB-2, as a single agent, is to block the export of lactate from the cells which results in accumulation of lactate and increased acidity within the cancer cells. However, this increased intracellular acidity of lactate may be neutralized by an increased amount of ammonia generated by the upregulation of glutamine metabolism and glutaminase activity in some tumors, especially in p53 mutant basal TNBC cells. On the other hand, although some of the basal type TNBC cells are sensitive to a glutaminase inhibitor alone, a considerable percentage of these cancers may manage to escape the harm of this drug by switching to a higher rate of import and metabolism of glucose. Thus, the combination of an MCT4 inhibitor and GLS1 inhibitor may solve this problem via restricting the metabolic flexibility of these cancer cells. The data herein indicates that treating p53 mutant basal TNBC cells in combination with blocking the export of lactate with CB-2 and inhibiting GLS1 with CB-839 elicits a great synergistic inhibitory effect, causing a significant growth inhibition in both cancer cells that are originally not sensitive to a glutaminase inhibitor or an MCT4 inhibitor alone and that originally show some sensitivity to the glutaminase inhibitor. Furthermore, this combination treatment is less toxic to normal cells (MCF-10A) because the energy source of normal cells depends primarily on TCA oxidative phosphorylation of glucose.

Example 2

Treatment with CB-1, CB2 or CB3 Inhibits Tumor Growth in a Mouse Cancer Model.

The anti-tumor effects of the MCT4 inhibitors CB-1, CB-2 and/or CB-3 were evaluated in nude mice implanted with human triple negative breast cancer (TNBC) cells (MDA-MB-231). For TNBC xenograft tumor models, MDA-MB-231 ($5 \times 10^6$) cancer cells were injected subcutaneously into the flanks of female athymic nude mice (nu/nu, 4 weeks old). Two weeks after the injection of cancer cells, xenograft tumors were found in the injection site. Tumor dimensions were measured, and volume was calculated by length (L), width (W), and height (H) using the formula (volume=$\pi/6 \times L \times W \times H$). After the tumors reached a volume of 50 mm$^3$, the mice were injected intraperitoneally with 20 mg/kg CB-1, CB-2, CB-3 or with the vehicle solution (DMSO; i.e., Control) for up to 4 weeks. The MCT4 inhibitors were injected daily for 5 days and then mice were rested for 2 days. CB-2 and CB-3 strikingly reduced the size and weight of MDA-MB-231 tumors in the xenografted mouse models without affecting body weight of the mice (FIG. 8A-C and FIG. 9A-C). Further, there were no detectable signs of systemic toxicity, implying minimal off-target or nonspecific effects of CB-2 and CB-3 in vivo. CB-1 also significantly inhibited tumor growth. However, after 18 days of injection the mice began to lose weight, suggesting that CB-1 may have certain toxicity. These results demonstrate that CB-1, CB-2 and CB-3 are capable of inhibiting TNBC xenograft tumor growth in vivo consistent with the in vitro activity observed using cell lines.

All animal studies were performed in accordance with the guidelines approved by the Institutional Animal Care and Use Committee of Charles Drew University of Medicine and Science.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features described herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an amount that is "less than" includes any non-zero amount less than a recited reference number.

Reference to a series of ranges includes ranges which combine the values of the boundaries of different ranges within the series. Thus, to illustrate reference to a series of ranges, for example, of 1-10 and 10-20, includes ranges of 1-20.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally described herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless described herein.

The technology illustratively described herein suitably can be practiced in the absence of any element(s) not specifically described herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 80%, at least 85%, at least 90%, at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

What is claimed is:

1. A pharmaceutical composition comprising a compound having the structure of formula Ill, or a salt thereof:

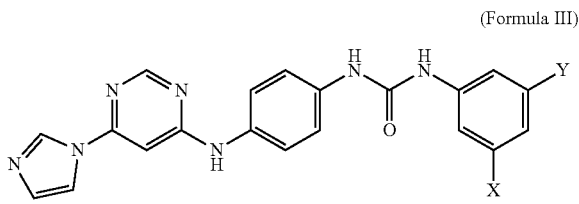

(Formula III)

wherein X and Y are independently selected from hydrogen, chlorine, fluorine, bromine and iodine, and the pharmaceutical composition comprises one or more pharmaceutically acceptable excipients or additives.

2. The pharmaceutical composition of claim 1, wherein X and Y are fluorine.

3. The pharmaceutical composition of claim 1, wherein the pharmaceutical composition is configured for, or formulated for, oral or parenteral administration.

4. A method of treating a cancer that expresses MCT4 in a subject in need thereof, comprising administering to the subject a therapeutically effective amount of the pharmaceutical composition of claim 1.

5. The method of claim 4, further comprising administering a therapeutically effective amount of metformin to the subject.

6. The method of claim 4, wherein the subject is human.

7. A kit comprising the pharmaceutical composition of claim 1.

8. The method of claim 4, wherein the cancer is selected from the group consisting of a carcinoma, sarcoma, neuro neoplasia, lymphoma, myeloma, leukemia, melanoma, mesothelioma, a solid tumor or a soft tissue tumor.

9. The method of claim 4, wherein the cancer is a breast cancer.

* * * * *